(12) United States Patent
Trieloff

(10) Patent No.: US 6,695,797 B2
(45) Date of Patent: Feb. 24, 2004

(54) FOOT SUPPORT SYSTEM

(76) Inventor: Rachelle D. Trieloff, 10801 Olive La., Bismarck, ND (US) 58503

( * ) Notice: Subject to any disclaimer, the term of this patent is extended or adjusted under 35 U.S.C. 154(b) by 0 days.

(21) Appl. No.: 10/142,856

(22) Filed: May 8, 2002

(65) Prior Publication Data

US 2002/0129821 A1 Sep. 19, 2002

Related U.S. Application Data

(63) Continuation-in-part of application No. 09/764,230, filed on Jan. 19, 2001.

(51) Int. Cl.[7] .............................. A61H 1/00; A61H 1/02; A61H 5/00
(52) U.S. Cl. ................................. 601/27; 602/5; 602/23; 602/27; 602/32; 602/36; 602/62; 602/65
(58) Field of Search ............................. 602/1, 3–5, 23, 602/27, 32–36, 60–62; 601/27

(56) References Cited

U.S. PATENT DOCUMENTS

| | | | | |
|---|---|---|---|---|
| 4,014,327 A | | 3/1977 | Spiro .......................... 128/165 |
| 4,073,490 A | * | 2/1978 | Feather ........................ 482/129 |
| 4,329,982 A | | 5/1982 | Heaney ........................ 128/80 |
| 4,459,980 A | | 7/1984 | Perser et al. ................... 128/80 |
| 4,566,447 A | | 1/1986 | Deis ............................. 128/80 |
| 5,203,754 A | | 4/1993 | Maclean ...................... 482/124 |
| 5,256,119 A | | 10/1993 | Tudor ........................... 482/74 |
| 5,277,699 A | | 1/1994 | Williamson ................... 602/28 |
| 5,291,904 A | * | 3/1994 | Walker ......................... 128/882 |
| 5,382,224 A | * | 1/1995 | Spangler ....................... 602/23 |
| 5,399,155 A | | 3/1995 | Strassburg et al. ............. 602/28 |
| 5,690,595 A | | 11/1997 | Quinones ..................... 482/124 |
| 5,718,673 A | | 2/1998 | Shipstead ..................... 602/27 |
| 5,720,042 A | * | 2/1998 | Wilkinson ....................... 2/69 |
| 5,807,218 A | | 9/1998 | Nagatomo .................... 482/124 |
| 5,843,010 A | | 12/1998 | Bodmer ....................... 602/27 |
| 6,004,282 A | | 12/1999 | Whitley ......................... 602/5 |
| 6,221,037 B1 | * | 4/2001 | Johnson et al. ................ 602/32 |

* cited by examiner

*Primary Examiner*—Nicholas D. Lucchesi
*Assistant Examiner*—L Amerson

(57) ABSTRACT

A foot support system for actively and passively supporting a foot of an individual suffering from drop foot. The foot support system includes an upper support removably attachable to the leg, a lower support removably attachable to the foot, and an elastic member attached between the upper support and the lower support for applying an upward force upon the distal portion of the foot. The upper support and the lower support preferably include an upper loop and a lower loop respectively for catchably receiving the elastic member. The elastic member may include an engaging member attached to a first end and a hook member attached to a second end thereof for selectively engaging one another.

3 Claims, 4 Drawing Sheets

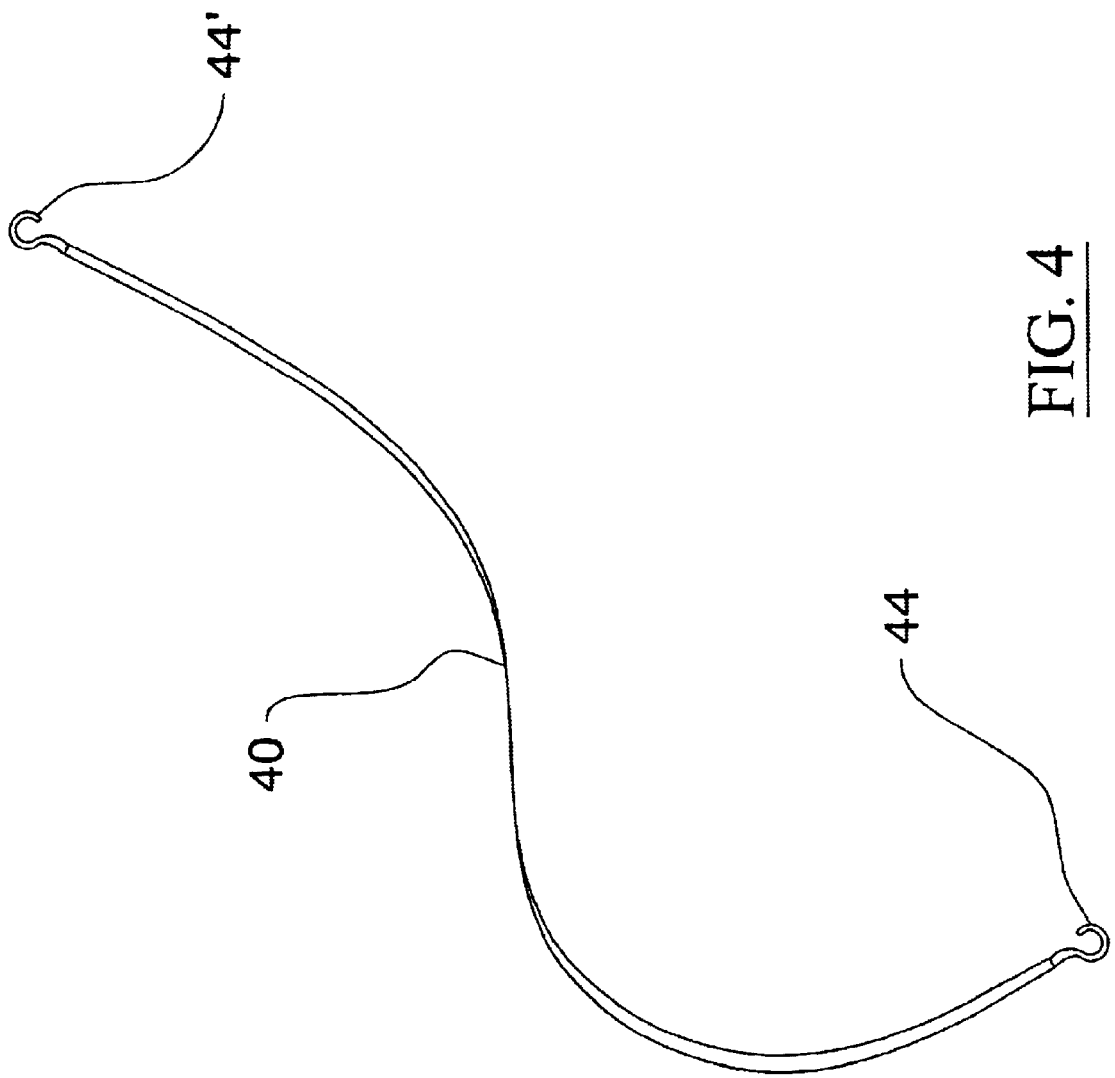

FOOT SUPPORT SYSTEM

CROSS REFERENCE TO RELATED APPLICATIONS

I hereby claim benefit under Title 35, United States Code, Section 120 of U.S. patent application Ser. No. 09/764,230 filed Jan. 19, 2001. This application is a continuation of the 09/764,230, filed Jan. 19, 2001 application. The Ser. No. 09/764,230 application is currently pending. The Ser. No. 09/764,230 application is hereby incorporated by reference into this application.

STATEMENT REGARDING FEDERALLY SPONSORED RESEARCH OR DEVELOPMENT

Not applicable to this application.

BACKGROUND OF THE INVENTION

1. Field of the Invention

The present invention relates generally to foot support devices and more specifically it relates to a foot support system for actively and passively supporting a foot of an individual suffering from drop foot.

A medical condition often times referred to as "foot drop" is a condition in which the foot hangs in a plantar-flexed position, due to various medical reasons such as a lesion of the peroneal nerve, muscle injury, neurofibromatosis, paralysis, stroke, leg injuries, bed ridden, or other medical conditions. An individual suffering from foot drop loses the ability to maintain the distal portion of their foot in an upright 90-degree support position making it difficult for the individual to walk as the distal portion of the foot engages the ground in a dragging manner. Unless significant permanent physical damage exists, foot drop can be corrected by supporting the foot within the normal 90-degree angle position with respect to the lower leg. Hence, there is a need for a product that effectively supports the foot of an individual suffering from foot drop.

2. Description of the Related Art

Foot and ankle support devices: have been in use for years. A typical device utilized for supporting a foot in a 90-degree position is a conventional foot brace that is not movable. Since a conventional foot brace does not allow for movement of the, foot, the individual is unable to exercise or move the foot muscles thereby weakening the foot muscles. Another problem with conventional foot braces is that they tend to be awkward and bulky for the individual to wear during normal everyday activities.

Additional products have been developed that attempt to assist in the support of the foot in a desired position such as but not limited to foam foot supports. As with conventional foot braces, these products are not effective in allowing movement of the foot and instead rely upon maintaining the foot within a stationary position which is not conducive for healing of the underlying medical problem.

Examples of patented devices which are related to the present invention include U.S. Pat. No. 5,718,673 to Shipstead; U.S. Pat. No. 5,807,218 to Nagatomo; U.S. Pat. No. 4,459,980 to Perser et al; U.S. Pat. No. 5,256,119 to Tudor; U.S. Pat. No. 4,014,327 to Spiro; U.S. Pat. No. 5,690,595 to Quinones; U.S. Pat. No. 5,399,155 to Strassburg et al; U.S. Pat. No. 4,566,447 to Deis; U.S. Pat. No. 4,329,982 to Heaney; U.S. Pat. No. 5,843,010 to Bodmer; U.S. Pat. No. 6,004,282 to Whitley; U.S. Pat. No. 5,277,699 to Williamson; and U.S. Pat. No. 5,203,754 to Maclean.

While these devices may be suitable for the particular purpose to which they address, they are not as suitable for actively and passively supporting a foot of an individual suffering from drop foot. Conventional foot braces only maintain the foot within a stationary position and do not allow for movement of the foot to assist in the medical recovery of the individual.

In these respects, the foot support system according to the present invention substantially departs from the conventional concepts and designs of the prior art, and in so doing provides an apparatus primarily developed for the purpose of actively and passively supporting a foot of an individual suffering from drop foot.

BRIEF SUMMARY OF THE INVENTION

In view of the foregoing disadvantages inherent in the known types of foot braces now present in the prior art, the present invention provides a new foot support system construction wherein the same can be utilized for actively and passively supporting a foot of an individual suffering from drop foot.

The general purpose of the present invention, which will be described subsequently in greater detail, is to provide a new foot support system that has many of the advantages of the foot supports mentioned heretofore and many novel features that result in a new foot support system which is not anticipated, rendered obvious, suggested, or even implied by any of the prior art foot braces, either alone or in any combination thereof.

To attain this, the present invention generally comprises an upper support removably attachable to the leg, a lower support removably attachable to the foot, and an elastic member attached between the upper support and the lower support for applying an upward force upon the distal portion of the foot. The upper support and the lower support preferably include an upper loop and a lower loop respectively for catchably receiving the elastic member. The elastic member may include an engaging member attached to a first end and a hook member attached to a second end thereof for selectively engaging one another.

There has thus been outlined, rather broadly, the more important features of the invention in order that the detailed description thereof may be better understood, and in order that the present contribution to the art may be better appreciated. There are additional features of the invention that will be described hereinafter and that will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of the description and should not be regarded as limiting.

A primary object of the present invention is to provide a foot support system that will overcome the shortcomings of the prior art devices.

A second object is to provide a foot support system for actively and passively supporting a foot of an individual suffering from drop foot.

Another object is to provide a foot support system that does not interfere with everyday activities of the user.

A further object is to provide a foot support system that maintains a foot within an approximately 90-degree angle with respect to a leg.

Another object is to provide a foot support system that prevents the onset of foot drop for bed ridden individuals.

A further object is to provide a foot support system that simultaneously provides support to a foot while providing physical exercise for the foot by providing resistance training.

Another object is to provide a foot support system that does not maintain the foot in a stationary and non-movable position.

An additional object is to provide a foot support system that provides therapy to the foot and leg muscles.

A further object is to provide a foot support system that is lightweight and non-obtrusive.

Another object is to provide a foot support system that allows an individual suffering from drop foot to walk freely.

Other objects and advantages of the present invention will become obvious to the reader and it is intended that these objects and advantages are within the scope of the present invention.

To the accomplishment of the above and related objects, this invention may be embodied in the form illustrated in the accompanying drawings, attention being called to the fact, however, that the drawings are illustrative only, and that changes may be made in the specific construction illustrated and described within the scope of the appended claims.

BRIEF DESCRIPTION OF THE DRAWINGS

Various other objects, features and attendant advantages of the present invention will become fully appreciated as the same becomes better understood when considered in conjunction with the accompanying drawings, in which like reference characters designate the same or similar parts throughout the several views, and wherein:

FIG. 4 is a perspective view of the elastic member having two opposing hook members.

DETAILED DESCRIPTION OF THE INVENTION

Figure 1:
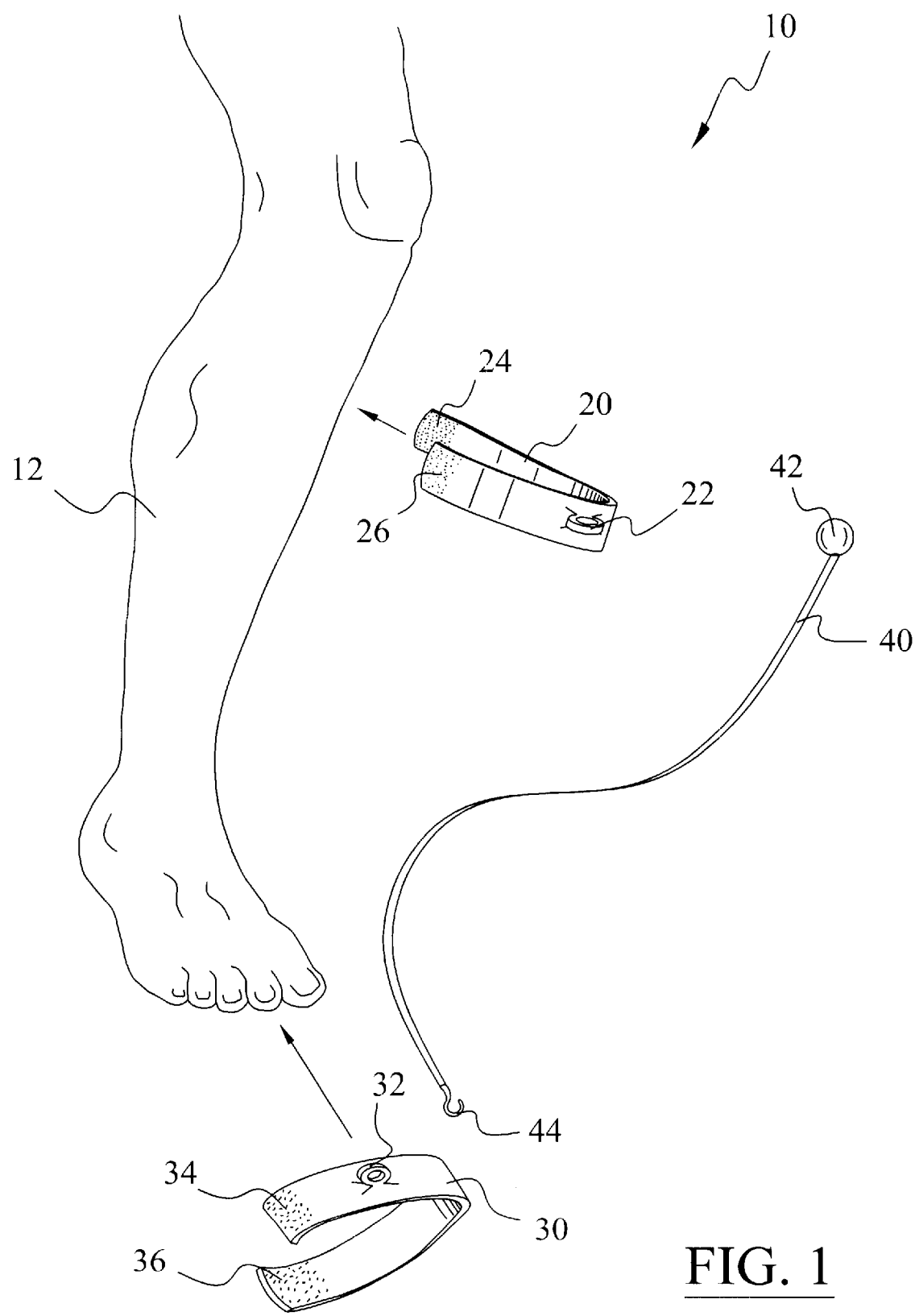
FIG. 1 is an exploded upper perspective view of the present invention with respect to a leg and foot of an individual.
Figure 2:
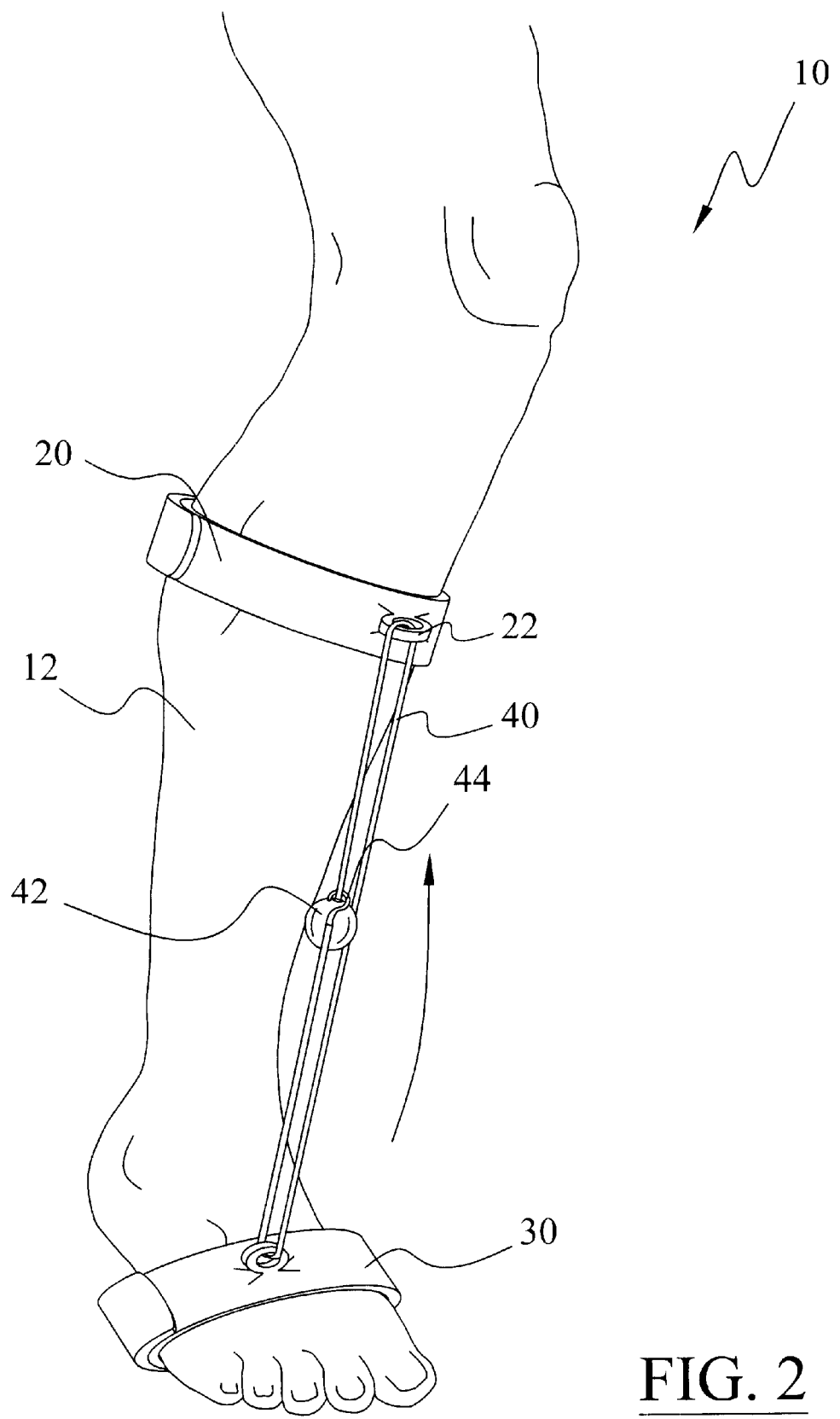
FIG. 2 is an upper perspective view of the present invention attached to the leg and foot of an individual.
Figure 3:
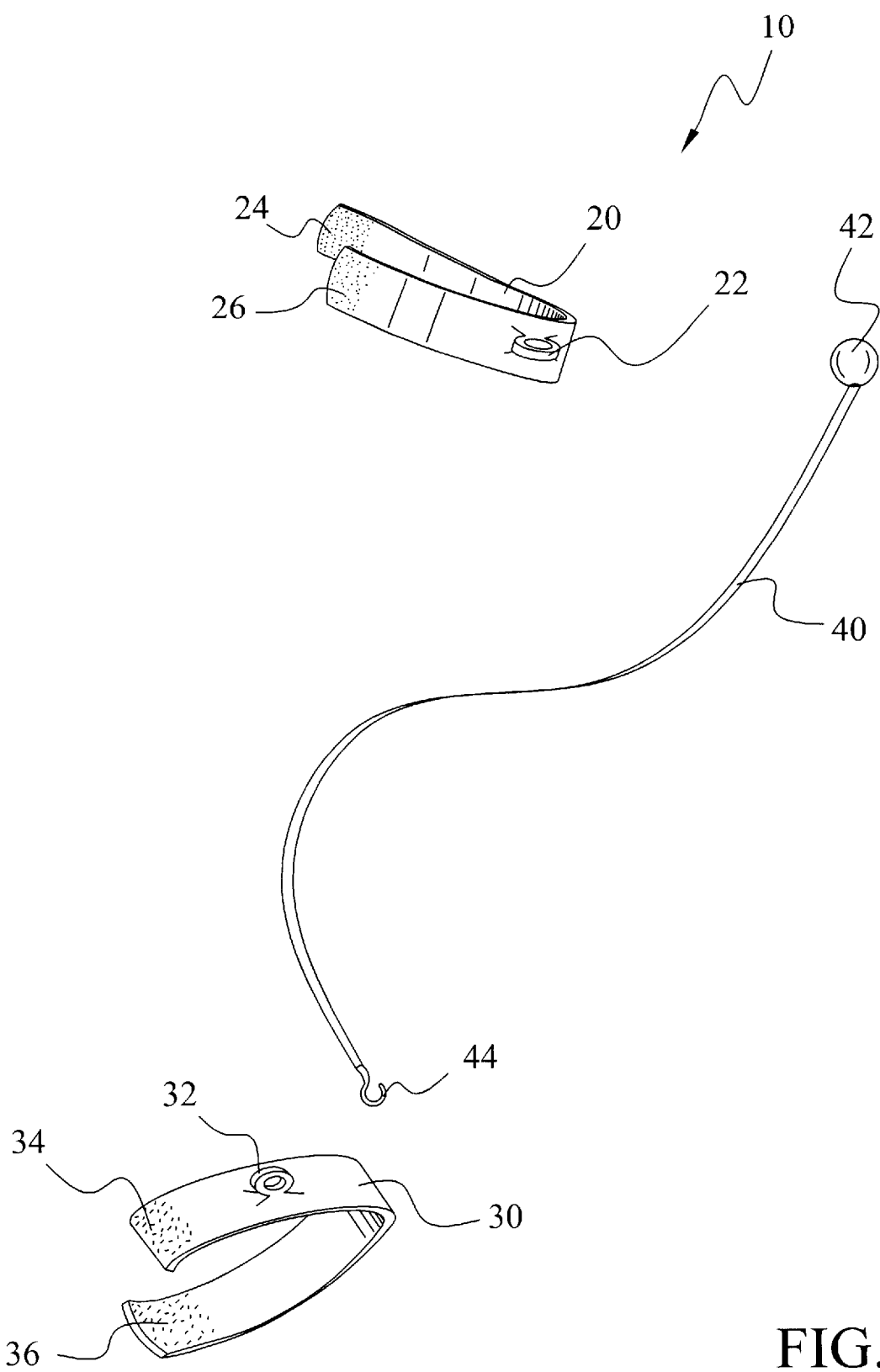
FIG. 3 is an exploded upper perspective view of the present invention.

Turning now descriptively to the drawings, in which similar reference characters denote similar elements throughout the several views, FIGS. 1 through 3 illustrate a foot support system 10, which comprises an upper support 20 removably attachable to the leg 12, a lower support 30 removably attachable to the foot, and an elastic member 40 attached between the upper support 20 and the lower support 30 for applying an upward force upon the distal portion of the foot. The upper support 20 and the lower support 30 preferably include an upper loop 22 and a lower loop 32 respectively for catchably receiving the elastic member 40. The elastic member 40 may include an engaging member 42 attached to a first end and a hook member 44 attached to a second end thereof for selectively engaging one another.

As shown in FIGS. 1 through 3 of the drawings, the upper support 20 is comprised of a collar structure that is removably attachable about the leg 12 of the user. The upper support 20 is preferably comprised of a flexible strap structure, however various other structures may be utilized to construct, the upper support 20. The upper support 20 may be comprised of various types of materials including but not limited to plastic, fabric, metal and other types of materials. The upper support 20 may be comprised of a rigid or flexible structure. In an alternative embodiment, the upper support 20 is comprised of a solid loop structure having an elastic structure that is slipped over the foot and leg 12 of the user to the desired position.

As shown in FIGS. 1 and 3 of the drawings, a first distal end of the upper support 20 includes a first upper fastener 24. A second distal end of the upper support 20 includes a second upper fastener 26 that is removably attachable to the first upper fastener 24 thereby allowing for secure fastening of the upper support 20 to the leg 12 at a desired position. The first upper fastener 24 and the second upper fastener 26 may be comprised of various fastening structures such as but riot limited to adhesive, hook and loop fastener, buckle, snap button, or slot button.

As shown in FIGS. 1 through 3 of the drawings, an upper loop 22 is attached to the outer portion of the upper support 20. The elastic member 40 is attached to the upper loop 22 during usage thereof as shown in FIG. 2. Various other structures may be utilized for engaging the elastic member 40 to the upper support 20.

As shown in FIGS. 1 through 3 of the drawings, the lower support 30 is comprised of a collar structure similar to the upper support 20 that is rermovably attachable about the foot of the user. The lower support 30 is preferably comprised of a flexible strap structure, however various other structures may be utilized to construct the lower support 30. The lower support 30 may be comprised of various types of materials including but not limited to plastic, fabric, metal and other types of materials. The lower support 30 may be comprised of a rigid or flexible structure. In an alternative embodiment, the lower support 30 is comprised of a solid loop structure having an elastic structure that is slipped over the foot of the user to the desired position.

As shown in FIGS. 1 and 3 of the drawings, a first distal end of the lower support 30 includes a first lower fastener 34. A second distal end of the lower support 30 includes a second lower fastener 36 that is removably attachable to the first lower fastener 34 thereby allowing for secure fastening of the lower support 30 to the foot at a desired position. The first lower fastener 34 and the second lower fastener 36 may be comprised of various fastening structures such as but not limited to adhesive, hook and loop fastener, buckle, snap button, or slot button.

As shown in FIGS. 1 through 3 of the drawings, a lower loop 32 is attached to the outer portion of the lower support 30. The elastic member 40 is attached to the lower loop 32 opposite of the upper loop 22 during usage thereof as shown in FIG. 2. Various other structures may be utilized for engaging the elastic member 40 to the lower support 30.

As illustrated in FIGS. 1 and 3 of the drawings, the elastic member 40 is comprised of an elongate structure having an engaging member 42 at one end and a hook member 44 at an opposing end thereof. The elastic member 40 is stretchable to various lengths for providing a consistent upward force upon the foot thereby maintaining the foot in a desired ninety-degree angle with respect to the leg 12 as shown in FIG. 2 of the drawings.

The engaging member 42 may be comprised of various structures capable of receiving the hook member 44 as shown in FIGS. 1 through 3 of the drawings. FIGS. 1 through 3 illustrate the engaging member 42 as having a spherical structure, however various other structures may be utilized to construct the engaging member 42. FIGS. 1 through 3 further illustrate the hook member 44 having an open C-shaped end for catchably engaging the elastic member 40 adjacent the engaging member 42. The elastic member 40 may include two opposing catch members, such as hook members 44, 44' as shown in FIG. 4 of the drawings, that directly catch the loops 22, 32 instead of looping the elastic member 40 through the loops 22, 32.

In use, the user first secures the upper support 20 upon a desired location of the leg 12 as shown in FIGS. 1 and 2 of the drawings. The user preferably secures the upper support 20 upon or above the calf in a snug manner to prevent downward movement thereof. The user then secures the lower support 30 upon the foot in a desired location as illustrated in FIG. 2 of the drawings. The user then extends the elastic member 40 through the upper loop 22 and the lower loop 32 as shown in FIG. 2 of the drawings. The user then connects the hook member 44 about the elastic member 40 adjacent the engaging member 42 as further shown in FIG. 2 of the drawings. In an alternative embodiment where the elastic member 40 has two opposing connecting members that directly connect to the loops 22, 32, the user would simply connect the opposing ends of the elastic member 40 directly to the loops 22, 32. After the elastic member 40 has been attached and is in a state of tension, the upward force of the elastic member 40 upon the lower support 30 draws the foot upwardly to an approximately ninety-degree angle, With respect to the leg 12 during relaxation of the leg 12 and foot. When the user desires to walk or exercise the leg 12, the user then extends their foot downwardly thereby extending the elastic member 40 followed by relaxing the leg 12 which allows the elastic member 40 to draw the foot back upwardly to the approximately ninety-degree angle. This process continues until the foot and leg 12 are healed sufficiently to prevent the drop foot condition.

As to a further discussion of the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed to be within the expertise of those skilled in the art, and all equivalent structural variations and relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

I claim:

1. A foot support system for movably supporting a foot in a traverse with respect to a leg, comprising:

an upper support removably attachable to an upper portion of a leg;

an upper loop attached to said upper support;

a lower support removably attachable to a foot;

a lower loop attached to said lower support;

an elastic member connectable between said upper loop and said lower loop in a tensioned manner; and an engagement member attached to a first end of said elastic member and a hook member attached to a second end of said elastic member, wherein said elastic member is extendable within said lower loop and said upper loop with said hook member selectively engageable to said engaging member;

wherein said engagement member has a body larger than an opening within said hook member.

2. The foot support system of claim 1, wherein said upper support has a first end and a second end with a first upper fastener and a second upper fastener attached respectively thereto for allowing selective closing thereof upon a leg.

3. The foot support system of claim 1, wherein said engagement member has a spherical structure.

* * * * *